US010478062B2

(12) United States Patent
Xie et al.

(10) Patent No.: US 10,478,062 B2
(45) Date of Patent: Nov. 19, 2019

(54) OPTOMETRY APPARATUS CAPABLE OF MEASURING PARA-CENTRAL DEFOCUS

(71) Applicant: SUZHOU SEEHITECH EQUIPMENTS CO., LTD, Suzhou, Jiangsu (CN)

(72) Inventors: Pei Xie, Jiangsu (CN); Renyuan Chu, Jiangsu (CN); Baichuan Jiang, Jiangsu (CN); Xingtao Zhou, Jiangsu (CN); Qinmei Wang, Jiangsu (CN); Junwen Zeng, Jiangsu (CN); Ruihua Wei, Jiangsu (CN); Qin Jiang, Jiangsu (CN); Li Zhong, Jiangsu (CN); Ji Shen, Jiangsu (CN)

(73) Assignee: SUZHOU SEEHITECH EQUIPMENTS CO., LTD, Suzhou, Jiangsu (CN)

( * ) Notice: Subject to any disclaimer, the term of this patent is extended or adjusted under 35 U.S.C. 154(b) by 39 days.

(21) Appl. No.: 15/737,672

(22) PCT Filed: Aug. 16, 2016

(86) PCT No.: PCT/CN2016/095559
§ 371 (c)(1),
(2) Date: Dec. 18, 2017

(87) PCT Pub. No.: WO2016/202312
PCT Pub. Date: Dec. 22, 2016

(65) Prior Publication Data
US 2018/0153400 A1 Jun. 7, 2018

(30) Foreign Application Priority Data
Jun. 18, 2015 (CN) .......................... 2015 1 0341685

(51) Int. Cl.
A61B 3/12 (2006.01)
A61B 3/00 (2006.01)

(52) U.S. Cl.
CPC .............. A61B 3/12 (2013.01); A61B 3/0008 (2013.01)

(58) Field of Classification Search
CPC ......... A61B 3/14; A61B 3/102; A61B 3/0025; A61B 3/12; A61B 3/1025; A61B 3/0008;
(Continued)

(56) References Cited

U.S. PATENT DOCUMENTS

2003/0011745 A1  1/2003  Molebny et al.
2008/0123053 A1  5/2008  Mihashi et al.
(Continued)

FOREIGN PATENT DOCUMENTS

CN    1194131      9/1998
CN    101646382    2/2010
(Continued)

OTHER PUBLICATIONS

Written Opinion of the International Search Authority (ISA/237) for PCT/CN2016/095559—Chinese Patent Office; dated Dec. 22, 2016.
(Continued)

Primary Examiner — Collin X Beatty
Assistant Examiner — Grant A Gagnon
(74) Attorney, Agent, or Firm — Baker, Donelson, Bearman, Caldwell & Berkowitz, PC

(57) ABSTRACT

Disclosed is an optometry apparatus capable of measuring para-central defocus, comprising a diopter measurement module. The diopter measurement module comprises a first light source (1) emitting a first light beam. The optometry apparatus also comprises a scanning module for adjusting the position of a light spot formed on the retina by the first light beam. The scanning module comprises a first reflecting
(Continued)

mirror (3) and a second reflecting mirror (5) rotatably positioned in sequence in the emergent optical path of the first light source (1). The rotation axis of the first reflecting mirror (3) and the rotation axis of the second reflecting mirror (5) form therebetween an angle greater than 0 degree and less than 180 degrees.

9 Claims, 1 Drawing Sheet

(58) Field of Classification Search
CPC ..... A61B 3/1005; A61B 3/113; A61B 3/1225; A61B 3/0058; A61B 3/107; A61B 3/117; A61B 3/13; A61B 3/1015; A61B 3/145; A61B 3/10; A61B 3/0041; A61B 3/152; A61B 3/103; A61B 3/0033; A61B 3/0075; A61B 3/0091; A61B 3/112; A61B 3/18; A61B 5/0066; A61B 2576/02; A61B 3/005; A61B 3/101; A61B 3/1208; A61B 3/1241; A61B 3/125; A61B 3/158; A61B 5/0013; A61B 2560/0475; A61B 3/00; A61B 3/0083; A61B 3/028; A61B 3/032; A61B 3/11; A61B 3/111; A61B 3/1233; A61B 3/132; A61B 5/0075; A61B 5/489; A61B 2017/00716; A61B 2503/10; A61B 2503/20; A61B 2560/0223; A61B 2560/0228; A61B 2560/0233; A61B 2560/0266; A61B 2560/0271; A61B 3/0016; A61B 3/024; A61B 3/063; A61B 3/08; A61B 3/1035; A61B 3/1173; A61B 3/1176; A61B 3/1216; A61B 3/135; A61B 3/15; A61B 3/154; A61B 3/156; A61B 5/0022; A61B 5/0059; A61B 5/02416; A61B 5/0261; A61B 5/1075; A61B 5/1079; A61B 5/1103; A61B 5/1114; A61B 5/1116; A61B 5/1124; A61B 5/1128; A61B 5/1176; A61B 5/1455; A61B 5/165; A61B 5/18; A61B 5/4821; A61B 5/4848; A61B 5/486; A61B 5/6803; A61B 5/7275; A61B 5/7425; A61B 8/10; A61B 90/20; G01B 9/02091; G01B 9/02004; G01B 9/02035; G01B 9/02044; G01B 2290/65; G01B 9/02028; G01B 9/0203; G01B 11/02; G01B 11/06; G01B 9/02009; G01B 9/02025; G01B 9/02027; G01B 9/02038; G01B 9/02041; G01B 9/02042; G01B 9/02058; G01B 9/02069; G01B 9/02072; G01B 9/02074; G01B 9/02077; G01B 9/02087; G01B 9/0209; G01B 9/02092; G06T 2207/30041; G06T 7/0012; G06T 2207/10101; G06T 7/0016; G06T 2200/24; G06T 7/74; G06T 11/003; G06T 2207/10016; G06T 2207/10056; G06T 2207/20016; G06T 2207/20056; G06T 2210/41; G06T 3/4038; G06T 7/0014; G06T 7/11; G06T 7/246; G06T 7/30; G06T 7/32; G06T 7/337; G06T 7/64; G02B 21/0012; G02B 27/0093; G02B 27/0955; G02B 27/141; G02B 27/48; G02B 7/14; G02B 17/0642; G02B 17/0663; G02B 17/0856; G02B 17/0896; G02B 19/0014; G02B 2005/1804; G02B 2027/0123; G02B 2027/0138; G02B 2027/0178; G02B 21/0028; G02B 21/0032; G02B 21/14; G02B 21/16; G02B 21/22; G02B 23/2407; G02B 26/023; G02B 26/06; G02B 27/0018; G02B 27/01; G02B 27/0101; G02B 27/0172; G02B 27/1013; G02B 27/1086; G02B 27/4244; G02B 27/4288; G02B 5/1809; G02B 5/1866; G02B 5/32; G02B 7/28
USPC .......................................................... 351/206
See application file for complete search history.

(56) References Cited

U.S. PATENT DOCUMENTS

2014/0098345 A1* 4/2014 Cai ................... A61B 3/102
351/206
2015/0112899 A1* 4/2015 Dagum ............... A61B 5/6898
706/12

FOREIGN PATENT DOCUMENTS

| CN | 103142210 | 6/2013 |
|---|---|---|
| CN | 103153170 | 6/2013 |
| CN | 103989453 | 8/2014 |
| CN | 104095610 | 10/2014 |
| CN | 104540442 | 4/2015 |
| CN | 104905763 | 9/2015 |
| CN | 204765562 | 11/2015 |
| WO | 2004086962 | 10/2004 |

OTHER PUBLICATIONS

International Search Report (ISA/210) for PCT/CN2016/095559; dated Dec. 22, 2016.

* cited by examiner

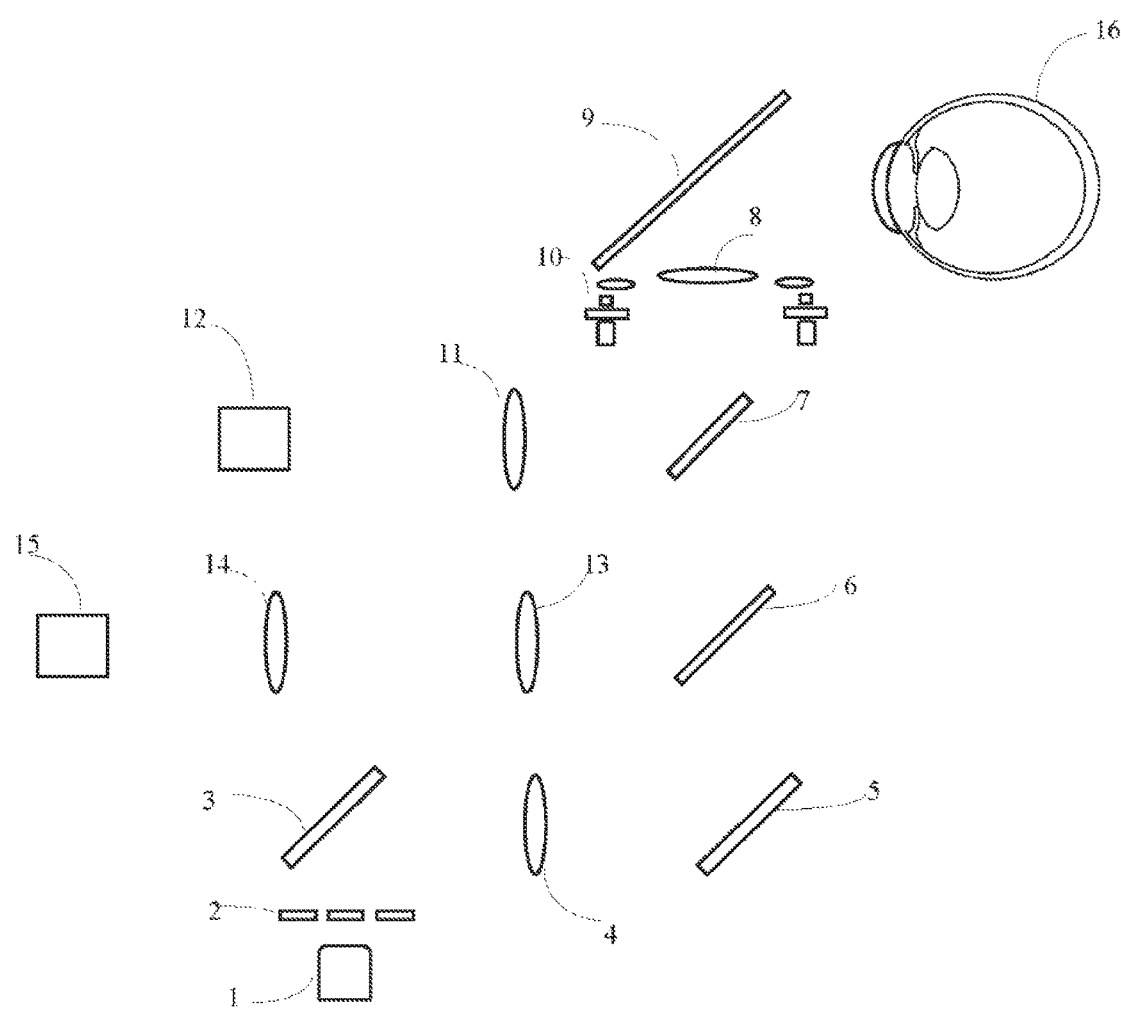

OPTOMETRY APPARATUS CAPABLE OF MEASURING PARA-CENTRAL DEFOCUS

CROSS REFERENCE TO RELATED APPLICATIONS

This application is a § 371 National Stage Application of PCT/CN2016/095559 filed Aug. 16, 2016, which claims priority to CN201510341685.0 filed Jun. 18, 2015, which are hereby incorporated by reference in their entirety.

TECHNICAL FIELD OF THE INVENTION

The present disclosure relates to the optometry field, in particular to an optometry apparatus capable of measuring para-central defocus.

BACKGROUND OF THE INVENTION

At present, when the optometry apparatus such as a traditional refractor proceeds optometry of a human eye, the light spot is projected on the macular area of the retina, the diopter measurement is only implemented on the macular area of the retina, and does not implemented on other area beside the macular area of the retina. The retina of a normal eye is spherical shaped, and when an object is imaged on the retina, the macular area of the retina and the macular periphery are just in the focal cambered surface of the human eye optical system. When the eye is abnormal, the cambered surface formed by the retina and the focal cambered surface of the human eye optical system do not coincide or have different curvatures. Due to that the traditional refractor only implements diopter measurement on the macular area, the object is imaged on the macular area after configuring glasses. If the curvature beside the macular area of the retina does not coincide with the focal cambered surface of the human eye optical system, employing the traditional refractor to configure glasses correct the diopter of the macular area, but the diopter of the retina beside the macular area has not been corrected yet. This forms para-central defocus, and if the para-central defocus cannot be corrected, it will stimulates the human eyes and further deepen the refractive error of human eyes, and the macular area will not see objects clearly, and it needs to conduct the optometry and configure the glasses again.

SUMMARY OF THE INVENTION

Aiming at the above mentioned problems, the purpose of the present invention is to provide an optometry apparatus capable of measuring para-central defocus.

To achieve the above aims, the technical scheme employed by the present disclosure is:

An optometry apparatus capable of measuring para-central defocus, comprises a diopter measurement module comprising a first light source emitting a first light beam, the optometry apparatus further comprises a scanning module for changing the position of the light spot formed on the retina by the first light beam, the scanning module comprises a first reflecting mirror and a second reflecting mirror which are rotatably positioned in sequence in the emergent optical path of the first light source, the rotation axis of the first reflecting mirror and the rotation axis of the second reflecting mirror form therebetween an angle greater than 0 degree and less than 180 degrees.

Preferably, the optometry apparatus comprises a fixation vision module enabling the eyeball of a subject in a relaxed state, the fixation vision module comprises a second dichroic mirror totally transmitting visible light and totally reflecting the first light beam, and the second dichroic mirror is disposed in the emergent light path of the first light source.

More preferably, the optometry apparatus further comprises a diaphragm, a first lens group, a beam splitter, a third lens group, a fourth lens group and a first photoelectric detector, the diaphragm, the first reflecting mirror, the first lens group, the second reflecting mirror, the beam splitter and the second dichroic mirror are disposed in the emergent light path of the first light source successively, the third lens group, the fourth lens group and the first photoelectric detector are disposed in the reflected light path of the beam splitter successively, and the first photoelectric detector is movably disposed in the light path relative to the fourth lens group.

Further, the optometry apparatus further comprises a corneal curvature measurement module, a first dichroic mirror, a fifth lens group and a second photoelectric detector, the corneal curvature measurement module comprises a second light source for emitting a second light beam, the first dichroic mirror totally transmits the first light beam and totally reflects the second light beam, the fifth lens group and the second photoelectric detector are disposed in the reflected light path of the first dichroic mirror successively, and the second dichroic mirror totally transmits visible light and totally reflects the first light beam and the second light beam.

More further, the second dichroic mirror is disposed in the emergent light paths of the first light source and the second light source, and the first dichroic mirror is disposed between the second dichroic mirror and the beam splitter.

More further, the optometry apparatus comprises a second lens group disposed between the first dichroic mirror and the second dichroic mirror.

Preferably, the wave length of the first light beam is 780-890 nm, and the wave length of the second light beam is 900-1000 nm.

Preferably, the optometry apparatus further comprises a first photoelectric detector movably disposed in the imaging light path of the first light beam, and a third optocoupler for detecting the position of the first photoelectric detector.

More preferably, the optometry apparatus further comprises a driving module for driving the first photoelectric detector to move and driving the first reflecting mirror and the second reflecting mirror to rotate, a data storage module for storing diopter and corneal curvature data, and a transmission module for transmitting the diopter and corneal curvature data to a cloud server.

Preferably, the rotation axis of the first reflecting mirror and the rotation axis of the second reflecting mirror are perpendicular to each other.

The above mentioned technical scheme employed by the present disclosure has the following advantages over the prior art: changing the propagation path of the first light beam by rotating the first reflecting mirror and the second reflecting mirror, and then changing the position of the light spot formed by the first light beam on the retina, two-dimensionally scanning the retina to obtain images reflected by respective areas of the retina, and thus implementing diopter measurement of the macular area and the areas beside the macular area of the retina, and achieving the diopter measurement of the para-central defocus.

BRIEF DESCRIPTION OF THE DRAWINGS

FIG. 1 is a schematic structure diagram of an optometry apparatus of the present disclosure.

Wherein, 1—first light source; 2—diaphragm; 3—first reflecting mirror; 4—first lens group; 5—second reflecting mirror; 6—beam splitter; 7—first dichroic mirror; 8—second lens group; 9—second dichroic mirror; 10—second light source; 11—fifth lens group; 12—second photoelectric detector; 13—third lens group; 14—fourth lens group; 15—first photoelectric detector; 16—human eye.

DETAILED DESCRIPTION OF EXEMPLARY EMBODIMENTS

In the following, the preferable embodiments of the present disclosure are explained in detail combining with the accompanying drawings so that the advantages and features of the present disclosure can be easily understood by the skilled persons in the art.

FIG. 1 shows an optometry apparatus capable of measuring para-central defocus of the present invention. Combining with FIG. 1, the optometry apparatus comprises a first light source 1, an annular diaphragm 2, a first reflecting mirror 3, a first lens group 4, a second reflecting mirror 5, a beam splitter 6, a first dichroic mirror 7, a second lens group 8, a second dichroic mirror 9, a second light source 10, a fifth lens group 11, a second photoelectric detector 12, a third lens group 13, a fourth lens group 14 and a first photoelectric detector 15.

In the FIG. 1 embodiment, the first light source 1, the annular diaphragm 2, the first lens group 4, the beam splitter 6, a first dichroic mirror 7, the third lens group 13, the fourth lens group 14 and the first photoelectric detector 15 form a diopter measurement module, for measuring the diopters of multiple different areas of the retina, including the macular area and the areas beside the macular area.

The first reflecting mirror 3 and the second reflecting mirror 5 form a scanning module for adjusting the position of the light spot formed on the retina by the diopter measurement module, so as to two-dimensionally scan the retina and to cause the light spots to be formed on different areas of the retina.

The second light source 10, the first dichroic mirror 7, the fifth lens group 11 and the second photoelectric detector 12 form a corneal curvature measurement module for measuring the corneal curvature;

The second dichroic mirror 9 forms a fixation vision module for enabling a human eye 16 in a relaxed state.

The first light source 1 emits a first light beam, and in the present embodiment, the first light source 1 employs a near-infrared LED light, and the first light beam is a near-infrared light beam with a wave length of 780-890 nm. The annular diaphragm 2, the first reflecting mirror 3, the first lens group 4, the second reflecting mirror 5 and the beam splitter 6 are disposed in the emergent light path of the first light source 1 successively. Wherein, the first reflecting mirror 3 and the second reflecting mirror 5 are driven by a motor to rotate, and the rotation axis of the first reflecting mirror 3 and the rotation axis of the second reflecting mirror 5 form therebetween an angle greater than 0 degree and less than 180 degrees, preferably 90 degrees, that is, the two rotation axes are perpendicular to each other, and the rotation axis of one of the first reflecting mirror 3 and the second reflecting mirror 5 is horizontally disposed, and the rotation axis of the other one is vertically disposed. By changing the angles of the first reflecting mirror 3 and the second reflecting mirror 5, the purpose of adjusting the propagation path of the first light beam is achieved, and as the motor continuously drives the first reflecting mirror 3 and the second reflecting mirror 5, the retina can be two-dimensionally scanned. During the rotation of the first reflecting mirror 3 and the second reflecting mirror 5, the mirror surface of the first reflecting mirror 3 and the mirror surface of the second reflecting mirror 5 are not parallel to each other.

The second light source 10 emits an annular second light beam, and in the present embodiment, the second light source 10 employs a set of infrared LED projection modules annularly arranged, and the emitted second light beam is an annular infrared light beam with a wave length of 900-1000 nm.

The second dichroic mirror 9 is disposed in the emergent light paths of the first light source 1 and the second light source 10, and used to reflect the near-infrared light emitted by the first light source 1 and the infrared light emitted by the second light source 10 to the human eye 16. The second dichroic mirror 9 totally transmits visible light and totally reflects infrared light and near-infrared light, during the measurement of the optometry apparatus, the subject gazes at distant objects through the second dichroic mirror 9 to let the subject's eye in the relaxed state.

The second lens group 8 is disposed between the second dichroic mirror 9 and the first dichroic mirror 7. The first dichroic mirror 7 totally transmits near-infrared light and totally reflects infrared light, and the fifth lens group 11 and the second photoelectric detector 12 are disposed in the reflecting light path of the first dichroic mirror 7 successively to collect infrared images reflected by the retina.

The first dichroic mirror 7 is disposed between the lens group and the beam splitter 6, and the third lens group 13, the fourth lens group 14 and the first photoelectric detector 15 are disposed in the reflecting light path of the beam splitter 6 successively to collect near-infrared images reflected by the retina.

The optometry apparatus further comprises a driving module. The driving module comprises a first motor and a second motor for driving the first reflecting mirror 3 and the second reflecting mirror 5 to rotate respectively, and a third motor for driving the first photoelectric detector 15 to move. In other implementations, the first reflecting mirror 3, the second reflecting mirror 5 and the first photoelectric detector 15 may also be driven by one or two motor(s) at the same time. The scanning module further comprises a first optocoupler and a second optocoupler for detecting the rotation angles of the output shafts of the first motor and the second motor respectively. The diopter measurement module further comprises a third optocouple for detecting the position of the first photoelectric detector 15. The first reflecting mirror 3 and the second reflecting mirror 5 are conjugate surfaces to each other and are both conjugate surfaces to the human pupil, as the first motor and the second motor driving the first reflecting mirror 3 and the second reflecting mirror 5 to rotate, the first light beam runs around the pupil and passes through the pupil totally, arrives the retina and forms light spots, so as to scan the retina. According to rotation angle data detected by the first optocoupler and the second optocoupler, control the rotation of the first motor and the second motor to ensure that both of the macular area and the areas beside the macular area of the retina can be scanned. Due to that the diopter values of different areas of the retina may be different, and the imaging positions of near-infrared images may also be different, the intervals between the near-infrared images formed by the fourth lens group 14 and the fourth lens group 14 are also different, and the third motor drives the first photoelectric detector 15 to move relative to the fourth lens group 14 via a transmission mechanism such as a screw, until the first photoelectric detector 15 collects the above mentioned near-infrared images. By recording the displacement distances of the screw, the optocouplers may obtain the positions of the first photoelectric detector 15 which are the imaging positions of the near-infrared images too, and different imaging positions of near-infrared images are correspond to different diopter values.

The corneal curvature measurement module employs a set of infrared LED projection modules annularly arranged to project an annular infrared spot, which is reflected by the mirror surface of the human cornea, and then is imaged on the second photoelectric detector 12 via a lens group, for collecting infrared images. The diopter measurement module employs near-infrared LED lights, which form an annular near-infrared light ring via the annular diaphragm 2, and the near-infrared light ring is projected on the retina and reflected by the retina, the reflected light ray is emitted from the human eye and imaged on the first photoelectric detector 15 through lens groups, and according to the detected position of the first photoelectric detector 15 which is the imaging position to, the diopter of the human eye can be calculated by calibration algorithm.

The optometry apparatus further comprises a data storage module and a wireless transmission module. The data storage module is used for storing diopter and corneal curvature data. The wireless transmission module is used for transmitting the diopter and corneal curvature data to a cloud server, for a long time storage facilitating follow-up checking and for doctors to analyze.

Above all, the present disclosure has the following characteristics:

Employing an open window design, that is, employing a dichroic mirror totally transmitting visible light and totally reflecting infrared light and near-infrared light, which enables the human eye in the relaxed state, and has a high reflectivity to infrared light and near-infrared light from the diopter measurement module and the corneal curvature measurement module, improving the use comfort and energy efficiency.

Disposing the scanning module in the emergent light path of the diopter measurement module, and driving the two sets of scanning reflecting mirrors of the scanning module to rotate through the motors, the two-dimensional scanning of the retina spot is achieved, and thus the diopter measurement of the macular area and the areas beside the macular area of the retina is achieved, the problem of incorrect diopter measurement of the para-central focus is solved, the diopter measurement of the para-central focus is achieved, and more scientific optometry guiding data is provided.

The two scanning reflecting mirrors of the scanning module are located at two different positions which are conjugate with the human pupil, which ensures the light ray runs around the pupil when the scanning module scans, and ensures all light rays transmit through the pupil, to two-dimensionally scan the retina.

The embodiments described above are only for illustrating the technical concepts and features of the present invention, are preferred embodiments, are intended to make those skilled in the art being able to understand the present invention and thereby implement it, and should not be concluded to limit the protective scope of this invention. Any equivalent variations or modifications according to the spirit of the present invention should be covered by the protective scope of the present invention.

The invention claimed is:

1. An optometry apparatus capable of measuring para-central defocus, comprising a first light source emitting a first light beam, wherein, the optometry apparatus further comprises a diaphragm, a first lens group, a beam splitter, a third lens group, a fourth lens group, a first photoelectric detector, a fixation vision module enabling an eyeball of a subject in a relaxed state, and a scanning module for changing a position of a light spot formed on the retina by the first light beam;

wherein, the first light source, the diaphragm, the first lens group, the beam splitter, the third lens group, the fourth lens group and the first photoelectric detector form a diopter measurement module;

the fixation vision module comprises a second dichroic mirror totally transmitting visible light and totally reflecting the first light beam;

the scanning module comprises a first reflecting mirror and a second reflecting mirror which are rotatably positioned in sequence in an emergent optical path of the first light source, the rotation axis of the first reflecting mirror and the rotation axis of the second reflecting mirror form therebetween an angle greater than 0 degree and less than 180 degrees;

the diaphragm, the first reflecting mirror, the first lens group, the second reflecting mirror, the beam splitter and the second dichroic mirror are disposed in the emergent light path of the first light source successively, the third lens group, the fourth lens group and the first photoelectric detector are disposed in a reflected light path of the beam splitter successively.

2. The optometry apparatus according to claim 1, wherein, the rotation axis of the first reflecting mirror and the rotation axis of the second reflecting mirror are perpendicular to each other.

3. The optometry apparatus according to claim 1, wherein, the optometry apparatus further comprises a third optocoupler for detecting a position of the first photoelectric detector.

4. The optometry apparatus according to claim 3, wherein, the optometry apparatus further comprises a driving module for driving the first photoelectric detector to move and for driving the first reflecting mirror and the second reflecting mirror to rotate, a data storage module for storing diopter and corneal curvature data, and a transmission module for transmitting the diopter and corneal curvature data to a cloud server.

5. The optometry apparatus according to claim 1, wherein, the first photoelectric detector is movably disposed in a light path relative to the fourth lens group.

6. The optometry apparatus according to claim 5, wherein, the optometry apparatus further comprises a second light source for emitting a second light beam, a first dichroic mirror, a fifth lens group and a second photoelectric detector, the first dichroic mirror totally transmits the first light beam and totally reflects the second light beam, the fifth lens group and the second photoelectric detector are disposed in a reflected light path of the first dichroic mirror successively, and the second dichroic mirror totally transmits visible light and totally reflects the first light beam and the second light beam.

7. The optometry apparatus according to claim 6, wherein, the wave length of the first light beam is 780-890 nm, and the wave length of the second light beam is 900-1000 nm.

8. The optometry apparatus according to claim 6, wherein, the second dichroic mirror is disposed in the emergent light paths of the first light source and the second light source, and the first dichroic mirror is disposed between the second dichroic mirror and the beam splitter.

9. The optometry apparatus according to claim 8, wherein, the optometry apparatus comprises a second lens group disposed between the first dichroic mirror and the second dichroic mirror.

* * * * *